United States Patent [19]

Rákóczi et al.

[11] Patent Number: 4,530,923
[45] Date of Patent: Jul. 23, 1985

[54] N-ACETAMILIDE, N-(PHENOXY-2-PROPANOL)- AND N-(PHENYLAMINO-2-PROPANOL)-CYCLICAMINES

[75] Inventors: József Rákóczi; Edit Berényi née Poldermann; Béla Fekete, all of Budapest; László Szekeres, Szeged; Gyula Papp, Szeged; Éva Keszthelyi née Udvary, Szeged, all of Hungary

[73] Assignee: Egyt Gyogyszervegyeszeti Gyar, Budapest, Hungary

[21] Appl. No.: 435,493

[22] Filed: Oct. 20, 1982

[30] Foreign Application Priority Data

Jun. 11, 1981 [HU] Hungary .................... 3308/81

[51] Int. Cl.³ .............. C07D 223/02; C07D 295/08; A61K 31/33; A61K 31/55
[52] U.S. Cl. .................. 514/183; 260/239 B; 514/212
[58] Field of Search ............ 260/239 B; 424/244

[56] References Cited

U.S. PATENT DOCUMENTS 3,723,476  3/1973  Nakanishi et al. ........... 544/146 X
4,191,765  3/1980  Fritsch et al. ............... 544/171 X

FOREIGN PATENT DOCUMENTS 2151587  4/1973  Fed. Rep. of Germany.
2300543  7/1974  Fed. Rep. of Germany.
3004360  9/1981  Fed. Rep. of Germany.

OTHER PUBLICATIONS

Chan et al., Chem. Abstracts, 63: 56301f (1965).
Iovu et al., Chem. Abstracts, 97: 174467a (1982).
Moehrle et al., Chem. Abstracts, 72: 90249b (1970).
Aktiebolag, Chem. Abstracts, vol. 65, (1966), Abstract 19941F.
Telc, et al., Chem. Abstracts, vol. 76, (1972), p. 375, Abstract 152718x.
Yang, et al., Chem. Abstracts, vol. 93, (1980), p. 527, Abstract 220697t.

Primary Examiner—Donald G. Daus
Assistant Examiner—William A. Teoli, Jr.
Attorney, Agent, or Firm—Karl F. Ross; Herbert Dubno

[57] ABSTRACT

The invention relates to new cyclic imines of the general formula (I),

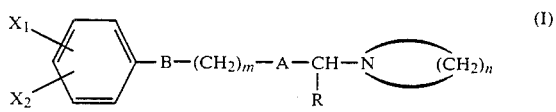

wherein
A represents carbonyl or hydroxymethylene,
B is oxygen or imino,
R stands for hydrogen or lower alkyl,
$X_1$ and $X_2$ may be the same or different and represent hydrogen, halogen, lower alkyl or alkoxy, amino or nitro,
n is 6 or 7, and
m is 0 or 1, and pharmaceutically acceptable acid addition salts and quaternary salts thereof. The invention relates further to a process for the preparation of said compounds, to pharmaceutical compositions containing said compounds as the active ingredient and to a process for the preparation of said pharmaceutical compositions.

The cyclic imine derivatives of the invention possess valuable antiarrhythmic properties and can be used to advantage in the treatment of cardiovascular diseases.

8 Claims, No Drawings

N-ACETAMILIDE, N-(PHENOXY-2-PROPANOL)- AND N-(PHENYLAMINO-2-PROPANOL)-CYCLICAMINES

The present invention relates to novel cyclic amine derivatives and to a process for their preparation. The invention also provides pharmaceutical compositions containing the said compounds.

Cardiovascular diseases nowadays are a leading cause of death. That is why great efforts are made all over the world for the preparation of new substances effective against these diseases.

Quinidine and derivatives thereof are still used for combatting cardiac rhythm disturbances [Br. Heart J. 38, 381 (1976)]. They are effective primarily in the treatment of arrhythmia, auricular flutter, fibrillation and paroxysmal tachycardia. However, these derivatives have toxic side-effects, namely they induce subjective hyperaesthesia, create vision problems, headache and nausea, and give rise to grave asthmatic symptoms.

The object of the present invention is to provide new and potent substances devoid of the above side-effects.

According to a feature of the present invention there are provided compounds of the formula (I),

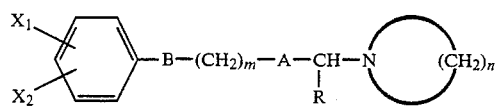

wherein
A represents carbonyl or hydroxymethylene,
B is oxygen or imino,
R stands for hydrogen or lower alkyl,
$X_1$ and $X_2$ may be the same or different and represent hydrogen, halogen, lower alkyl or alkoxy, amino or nitro,
n is 6 or 7, and
m is 0 or 1,
and pharmaceutically acceptable acid addition salts thereof.

The term "lower alkyl" means straight-chain or branched saturated aliphatic hydrocarbyl groups containing 1 to 4 carbon atoms, such as methyl, ethyl, n-propyl, isopropyl, isobutyl. The term "lower alkoxy" refers to straight-chained or branched alkylether groups containing 1 to 4 carbon atoms, such as methoxy, ethoxy, n-propoxy, isopropoxy, n-butoxy. The term "halogen atom" may stand for all the four halogen atoms, such as fluorine, chlorine, bromine or iodine.

In a preferred subgroup of the new compounds having the formula (I) $X_1$ and $X_2$ stand for a lower alkyl, preferably methyl, particularly in positions 6 and 7.

Those compounds of the formula (I) are also preferred, wherein A represents a hydroxymethylene group.

In a further preferred subgroup of the compounds of the formula (I) m is 1, and R represents hydrogen or alkyl, particularly methyl.

The following representatives of the compounds of the general formula (I) have the most valuable pharmaceutical activities:
1-(2,6-dimethylphenoxy)-3-hexamethyleneimino-propanol-2,
1-(2,6-dimethylphenoxy)-3-heptamethyleneimino-propanol-2,
1-hexamethyleneimino-3-(2,6-dimethylanilino)-propanol-2,
and pharmaceutically acceptable acid addition salts and quaternary salts of the above derivatives.

The acid addition salts of the compounds of the general formula (I) can be formed with pharmaceutically acceptable inorganic acids (e.g. hydrogen chloride, hydrogen bromide, sulfuric or nitic acid), or pharmaceutically acceptable sulfonic acids (e.g. benzenesulfonic, p-toluenesulfonic acid, etc.) or pharmaceutically acceptable carboxylic acids (e.g. lactic, fumaric, maleic, malic, mandelic, nicotinic acid). Of the pharmaceutically acceptable acid addition salts the hydrochlorides are of special interest.

The quaternary salts of the compounds of the formula (I) can be formed with pharmaceutically acceptable quaternizing agents (e.g. methyl iodide, ethyl iodide, etc.).

According to a further feature of the present invention there is provided a process for the preparation of cyclic imine derivatives of the general formula (I) and pharmaceutically acceptable acid addition salts and quaternary salts thereof, characterized in that a. to prepare a compound of the formula (I), in which A is a carbonyl group, B stands for an imino group and m is 0, a compound of the formula (II),

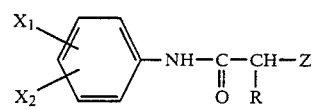

wherein R, $X_1$, $X_2$ are as defined above and Z is a leaving group,
is reacted with a cyclic imine of the formula (III),

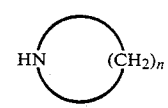

wherein n has the above defined meaning; or b. to prepare a compound of the formula (I), in which A is a hydroxymethylene group, B is an oxygen atom and n is 1,
b₁. a compound of the formula (IV),

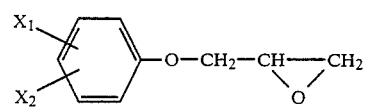

wherein $X_1$ and $X_2$ are as defined above,
is reacted with a cyclic imine of the formula (III), wherein n is as defined above; or
b₂. a compound of the formula (V),

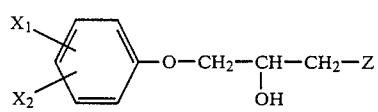

wherein $X_1$ and $X_2$ are as defined above, and Z is a leaving group,
is reacted with a cyclic imine of the formula (III), wherein n has the above defined meaning; or b$_3$. a compound of the formula (VI),

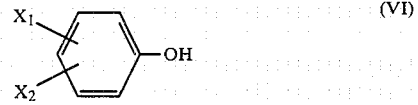

wherein $X_1$ and $X_2$ have the above defined meanings, is reacted with a compound of the formula (VII),

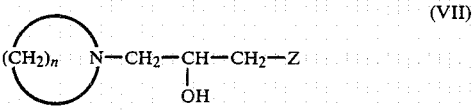

wherein n is as defined above, and Z represents a leaving group; or c. to prepare a compound of the formula (I), in which A stands for a hydroxymethylene group, B is an imino group and m is 1, c$_1$. a compound of the formula (VIII),

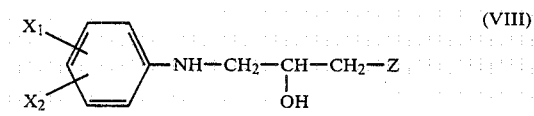

wherein $X_1$ and $X_2$ have the above defined meanings and Z is a leaving group,
is reacted with a cyclic imine of the formula (III), wherein n is as defined above; or c$_2$. an amine of the formula (IX),

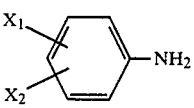

wherein $X_1$ and $X_2$ have the above-defined meanings, is reacted with a compound of the formula (VII), wherein n is as defined above,
and, if desired, converting the $X_1$ or $X_2$ group of the compound of the general formula (I) thus obtained into another $X_1$ or $X_2$ group, and, if desired, converting a compound of the general formula (I) thus obtained into a pharmaceutically acceptable acid addition salt or quaternary salt.

According to method a. of the process according to the invention compounds of the formula (I), wherein A represents a carbonyl group, B stands for an imino group, and m is 0, are produced by reacting a compound of the formula (II) with a compound of the formula (III). In the starting substance of the general formula (II) Z represents a leaving group, preferably a halogen atom (e.g. chlorine or bromine, particularly chlorine) or a sulfonyloxy group (e.g. an alkylsulfonyloxy group, preferably mesyloxy; or an arylsulfonyloxy group, preferably benzoylsulfonyloxy, p-tosyloxy or p-bromophenylsulfonyloxy group). The reaction is preferably carried out in a protic or apolarprotic solvent. Aliphatic alcohols (such as methanol, ethanol, isopropanol, etc.), dimethylformamide, di-methyl acetamide, etc. are preferably used for this purpose. The reaction can be performed in a wide temperature range, e.g. from 0° C. to 160° C., preferably at the boiling point of the solvent.

According to method b. of the process of the invention compounds of the formula (I), wherein A is a hydroxymethylene group, B represents an oxygen atom and m is 1 are prepared. This process can be performed in three different ways:

According to variant b$_1$. of the process compounds of the general formula (IV) are reacted with cyclic imines of the general formula (III). The reaction is preferably performed in a solvent. Aliphatic alcohols (such as methanol, ethanol, isopropanol), aromatic hydrocarbons (such as benzene, toluene, xylene), dimethylformamide, dimethyl acetamide are preferably used as solvent, but an excess of the cyclic imine of the formula (III) can also serve as solvent. The reaction is preferably performed at higher temperatures, particularly at the boiling point of the reaction mixture. When carrying out the reaction in an excess of the cyclic imine, the reaction is performed at 140° to 150° C.

According to variant b$_2$. of the process compounds of the formulae (V) and (VI) are reacted. In the formula (V) Z represents a leaving group. As preferable leaving groups, those listed in connection with the compound of the formula (II) are used. The reaction is preferably carried out in a solvent (e.g. in an aliphatic alcohol or aromatic hydrocarbon) at higher temperatures (60° to 160° C.), particularly at the boiling point of the reaction mixture. An excess of the cyclic imine can also serve as solvent.

In process variant b$_3$. of the invention a compound of the formula (VI) is reacted with a compound of the formula (VII). In the general formula (VII) of the starting substance Z represents a leaving group. As preferable leaving groups those listed in connection with the compound of the formula (II) are used. The reaction is preferably carried out in a solvent (such as aliphatic alcohols, aromatic hydrocarbons, etc.), at higher temperatures.

According to variant c. of the process according to the invention compounds of the formula (I), wherein A represents a hydroxymethylene group, B stands for an imino group and m is 1, are prepared. This reaction can be accomplished in two ways, namely by reacting compounds of the formulae (VIII) and (III) or by reacting compounds of the formulae (IX) and (VII). In the formulae (VII) and (VIII) Z is a leaving group. As preferable leaving groups those listed in connection with the compound of the formula (II) are used. The reactions are performed preferably in a solvent. For this purpose aliphatic alcohols, aromatic hydrocarbons, dimethylformamide, dimethyl sulfoxide or dimethyl acetamide can be used. An excess of the cyclic imine of the formula (III) and that of the amine of the general formula (IX) can also serve as solvent. The reaction is accomplished preferably at higher temperatures, e.g. between 100° C. and 160° C., particularly at the boiling point of the reaction mixture.

If desired, the $X_1$ or $X_2$ group of the compound of the formula (I) thus obtained can be converted into another $X_1$ or $X_2$ group. These reactions can be carried out by methods known per se, e.g. a nitro group can be converted into an amino group by catalytic hydrogenation (palladium, platinum, Raney nickel, etc.).

The compounds of the formula (I) can be converted into pharmaceutically acceptable acid addition salts by methods known per se. The salt formation can be performed e.g. by reacting a base of the formula (I) with a molar equivalent of an acid in a solvent. The pharmaceutically acceptable acid addition salts of the compounds of the formula (I) can be produced also by liberating the base of the formula (I) from a pharmaceutically unacceptable acid addition salt with a strong base (e.g. alkali hydroxide) and then reacting it with a pharmaceutically acceptable acid.

The pharmaceutically acceptable quaternary salts of the compounds of the formula (I) can be prepared by known methods, namely by reacting a compound of the formula (I) with a suitable quaternizing agent (e.g. methyl iodide, ethyl iodide, etc.) in a solvent.

The compounds of the formula (II) used as starting substances are in part known derivatives (Dutch Patent Specification No. 96,283; French Patent Specification No. 2,043,469), the others can be produced by the general method described in J. Med. Chem. 22, 1171 (1979).

The cyclic imines of the formula (III) are commercially available products.

Certain compounds of the formula (IV) are known [Zsur. Obscsej Himii 27, 1223–6 (1975), others can be produced by the method described in the Japanese Patent Specification No. 52,105,137].

The compounds of the formula (V) are known and can be prepared by the method described in J. Chem. Soc. 1954, 1571–7. The compounds of the formulae (VI) and (IX) are commercially available products.

The compounds of the formula (VII) can be prepared by reacting the cyclic imines of the formula (III) with epichlorohydrine.

The compounds of the formula (VIII) are partly known and the method for the preparation thereof is published in J. Med. Chem. 10, (2) 285 (1967).

The compounds of the invention possess highly favorable antiarrhythmic properties, which were tested on cats having an average weight of 2.2 to 3.5 kg. The animals were anaesthetized with chloralose-urethane [50/30 mg/kg, i.v.]. The minimal strength of the current necessary to evoke the ventricular and auricular fibrillo-flutter, respectively, was followed by the method of Szekeres and al. [Szekeres, Méhes and Papp: Brit. J. Pharmacol. 17, 167 (1961); Szekeres and Papp: Experimental Cardiac Arrhythmias and Antiarrhythmic Drugs, Akadémiai Kiadó, Budapest, 1971; Szekeres and Papp: Experimental Cardiac Arrhythmias, Hdb. Exp. Pharmacol. XVI/3, 131, (1975).

The therapeutic indices related to the antiarrhythmic activity were calculated on the basis of the $LD_{50}/ED_{50}$ ratio, where $LD_{50}$ is the doses resulting in the death of the 50% of the animals (rats), and $ED_{50}$ is the dosis provoking a 50% rise in the electrical threshold for fibrillation on rats. The $LD_{50}$ values were determined on male Wistar rats weighing 180 to 220 g by the method of Litchfield and Wilcoxon [J. Pharmacol. Exp. Ther. 95, 49 (1949)].

The results are given in Table I:

TABLE I

| | | Auricle | | | Ventricle | |
| | | Therapeutic index | | | Therapeutic index | |
| Compound No. of Example | Relative activity+ | $LD_{50}:ED_{50}$ /i.v.//i.v./ | $LD_{50}:ED_{50}$ /p.os//i.v./ | Relative activity+ | $LD_{50}:ED_{50}$ /i.v.//i.v./ | $LD_{50}:ED_{50}$ /p.os//i.v./ |
|---|---|---|---|---|---|---|
| 5 | 7.14 | 13.3 | 189 | 8.04 | 7.7 | 110 |
| 6 | 12.50 | 23.9 | 1964 | 2.80 | 2.8 | 229 |
| 7 | 8.54 | 20.7 | 439 | 7.85 | 9.9 | 209 |
| Quinidine | 1.00 | 13.4 | 280 | 1.00 | 6.9 | 145 |

+Relative activity calculated from the antiarrhythmic activity [$ED_{50}$ mg/kg, i.v.] determined on cats by the fibrillation threshold method
The i.v. and p.os $LD_{50}$ values were determined on rats.

As the above data show, the antiarrhythmic activity of the new compounds of the invention surpasses that of the known quinidine both on ventricle and on auricle. The compound of Example 6 possesses the most preferable therapeutic index related to the supraventricular activity; it is about 1.8 times (i.v. toxicity) and 7 times (per os toxicity), respectively, higher than that of quinidine. On auricle the therapeutic indices of all the three compounds are lower than on ventricle. However, it should be mentioned that the quotient per os $LD_{50}$/i.v. $ED_{50}$ of the compound of Example 6 is about 1.6 times, the quotient i.v. $LD_{50}$/i.v. $ED_{50}$ of the compound of Example 7 is about 1.4 times higher than that of quinidine.

The compounds of Examples 5, 6 and 7, tested by heartelectrophysiological methods on an isolated rabbit heart preparation decrease the spontaneous frequency of right ventricle, increase the electric stimulus threshold, prolong the effective refractory period and also the time of stimulus conduction. The data referring hereto are given in Table II, in the percentage of the original values.

TABLE II

| Compound No. of Example | Concentration mg/l | Spontaneous frequency /right auricle/ | Time of the stimulus-conduction /left auricle/ | Effective refractory period | | Electrical threshold | |
| | | | | /left auricle/ | /papillary muscle/ | /left auricle/ | /papillary muscle/ |
|---|---|---|---|---|---|---|---|
| 5 | 0.2 | −4 ± 2 | +38 ± 10 | +10 ± 3 | +9 ± 5 | +24 ± 9 | +46 ± 18 |
| 6 | 0.2 | −7 ± 1 | +15 ± 3 | +3 ± 2 | +4 ± 2 | +19 ± 8 | +9 ± 4 |
| 7 | 0.5 | −9 ± 1 | +28 ± 8 | +11 ± 2 | +10 ± 2 | +25 ± 5 | +29 ± 4 |
| Quinidine | 5 | −12 ± 1 | +90 ± 8 | +32 ± 7 | +55 ± 9 | +120 ± 12 | +56 ± 6 |

On dogs anaesthetized with nembutal (35 mg/kg, i.v.) in an i.v. dosis of 0.5 to 2 mg/kg the compounds slightly decrease the arterial blood pressure. The compounds of Examples 5 and 6 decrease the coronary resistance, improve the oxygenization of the heart muscle, increase the blood flow of the artery femoralis, and the compound of Example 5 increases also the blood flow of arteria carotis.

In addition, the compound of Example 6 possesses a strong local anaesthetic effect, which—tested on the action potential of nervus ischiadicus of frog—is 2.7 times stronger than that of lidocaine.

According to a further feature of the present invention there are provided pharmaceutical compositions containing as active substance at least one of the compounds of the formula (I) or a pharmaceutically acceptable acid addition salt or quaternary salt thereof, along with an appropriate inert, non-toxic, solid or liquid carrier. The compositions of the invention can be formulated in solid (e.g. tablets, capsules, coated pills) or liquid (e.g. solutions, suspensions, emulsions) form.

The carriers may be such as generally used in pharmacy (e.g. starch, magnesium stearate, calcium carbonate, polyvinylpyrrolidone, gelatine, talcum, etc.). The compositions may also contain suitable additives (e.g. emulsifying, disintegrating, suspensing agents, buffers, etc.) and optionally further active substances. These pharmaceutical compositions can be administered orally, rectally or parenterally.

The preparation of the pharmaceutical compositions according to the invention is carried out by the methods generally applied in pharmacy.

The daily dosage in the case of humans is 10 to 200 mg i.v. and 100 to 6000 mg per os.

The invention is illustrated by the following Examples of non-limiting character:

EXAMPLE 1

Preparation of heptamethyleneimino-acetoxylidine 49.4 g (0.25 moles) of chloroacetoxylidine are dissolved in 170 ml of ethanol, the solution is heated to boiling, and 71.7 g (0.63 moles) of heptamethyleneimine are dripped into it within 2 hours, under stirring. The reaction mixture is boiled for 3 hours under stirring, then cooled to a temperature between 5° C. and 10° C. and alkalized with sodium hydroxide (pH=9). The separated white precipitate is filtered off and washed with water.

Yield: 61.5 g (89.8%)

When recrystallized from ethanol, the product melts at 86° to 87° C.

The base thus obtained is dissolved in ether and converted into its hydrochloride with ethanol. The snow-white powder-like salt melts at 167° to 169° C.

Analysis: $C_{17}H_{26}N_2O$: Calculated: C%=65.68 H%=8.76 N%=9.81 Cl%=11.40; Found: C%=65.71 H%=8.74 N%=8.97 Cl%=11.42.

$^1$H-NMR (CDCl$_3$): 1.5–1.8 (m 10, —CH$_2$—(CH$_2$)$_5$—CH$_2$), 2.15 (s 6, CH$_3$), 3.35(s 4, —CH$_2$—N—CH$_2$), 4.38 (s 2,

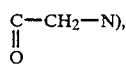

6.9 (s 3, ArH), 9.85 and 10.4 (s NH).

EXAMPLE 2

Preparation of hexamethyleneimino-acetoxylidine

One proceeds as described in Example 1, with the difference that hexamethyleneimine is used instead of heptamethyleneimine. In this way 60.0 g (92.3%) of hexamethyleneimino-acetoxylidine are obtained. When recrystallized from petroleum ether the product melts at 90° to 91° C.

The hydrochloride formed from the thus-obtained base melts at 179° to 180° C.

Analysis: $C_{16}H_{24}N_2O.HCl$ (Mol. weight: 296.84): Calculated: C%=64.74 H%=8.49 N%=9.44 Cl%=11.94; Found: C%=64.80 H%=8.20 N%=9.46 Cl%=12.01.

$^1$H-NMR (CDCL$_3$): 1.63 (s s, 8, —CH$_2$—(CH$_2$)$_4$—CH$_2$), 2.17 (s 6, CH$_3$), 3.35 (s, s 4,

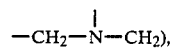

4.33 (s 2,

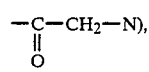

6.93 (s 3, ArH), 10.3 (s 1, NH).

EXAMPLE 3

Preparation of heptamethyleneimino-propionoxylidine 21.17 g (0.1 mole) of chloropropionoxylidine are dissolved in 150 ml of methyl cellosolve. 28.3 g (0.25 moles) of heptamethyleneimine are dropped to the solution, under reflux. The reaction mixture is refluxed for further 6 hours and allowed to stand overnight. The separated white, needleshaped crystals are filtered off.

Yield: 24.3 g (84.3%) M.p.: 132° to 133° C.

The hydrochloride salt melts at 227° to 230° C.

Analysis: $C_{18}H_{28}N_2O.HCl$ (Mol. weight: 324.9): Calculated: C%=66.54 H%=9.00 N%=8.62 Cl%=10.9; Found: C%=66.74 H%=9.05 N%=8.51 Cl%=10.85.

$^1$H-NMR (CDCL$_3$): 1.82 (d 3, CH$_3$—CH), 1.6–2.0 (m 10, —CH$_2$—(CH$_2$)$_5$—CH$_2$), 2.18 (s 6, CH$_3$—O), 3.6 (s s4,

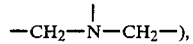

5.15 (m 1,

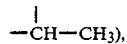

6.9 (s 3, ArH), 9.9, 10.4 (s a,

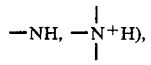

EXAMPLE 4

Preparation of hexamethyleneimino-propionoxylidine

One proceeds as described in Example 3, with the difference that hexamethyleneimine is used instead of heptamethyleneimine.

Yield: 93%

When recrystallized from a mixture of water and ethanol, the base melts at 101° to 102° C. The hydrochloride salt melts at 208° to 210° C.

Analysis: $C_{17}H_{26}N_2O.HCl$ (Mol. weight: 310.9): Calculated: C%=65.68 H%=8.76 N%=9.10

Cl%=11.41; Found: C%=65.93 H%=8.82 N%=8.97 Cl%=11.30.

¹H-NMR (CDCl₃): 1.88 (d 3, CH₃—CH—), 1.66–2.0 (m 8, —CH₂—(CH₂)₄—CH₂—), 2.23 (s 6, CH₃), 3.65 (s s 4, —CH₂—N—CH₂), 5.15 (m 1, —CH—CH₃), 6.97 (s 3, ArH), 10.3, 10.8 (s s, NH, —NH).

EXAMPLE 5

Preparation of 1-(2,6-dimethylphenoxy)-3-hexamethyleneimino-propanol-2

A mixture of 21.2 g (0.12 moles) of 2.6-dimethylepoxypropane and 14.88 g (0.15 moles) of hexamethyleneimine is held at 140° to 145° C. for 3.5 hours. Then the excess of hexamethyleneimine is distilled off from the thus-obtained brown solution. The residual brown oil is poured onto 500 ml of icy water, where the desired product solidifies.

Yield: 29.4 g (88.5%).

When recrystallized from a mixture of ethanol and water, the product melts at 40° to 42° C.

The hydrochloride of the thus-obtained base melts at 132° to 134° C.

Analysis: C₁₇H₂₇NO₂.HCl (Mol. weight: 313.88): Calculated: C%=65.05 H%=8.99 N%=4.46 Cl%=11.30; Found: C%=65.33 H%=9.12 N%=4.42 Cl%=11.19.

¹N-NMR (CDCl₃): 1.7–2.0 (m 8, —CH₂—(CH₂)₄—CH₂), 2.2 (s 6, CH₃), 3.3–3.6 (m 6,

—CH₂—N—CH₂—), 3.8 (d 2, —CH₂—O), 4.5

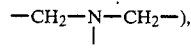

(m 1, —CH—), 5.5 (s s 1, OH), 6.9 (s 3, ArH).

EXAMPLE 6

Preparation of 1-(2,6-dimethylphenoxy)-3-heptamethyleneimino-propanol-2

One proceeds as described in Example 5, with the difference that heptamethyleneimine is used instead of hexamethyleneimine.

Yield: 91%

The hydrochloride melts at 138° to 140° C.

Analysis: C₁₈H₂₈NO₂.HCl (Mol. weight: 327.9): Calculated: C%=65.93 H%=9.22 N%=4.27 Cl%=10.81; Found: C%=65.87 H%=9.55 N%=4.25 Cl%=10.80.

¹H-NMR (CDCl₃): 1.5–2.2 (m 10, —CH₂—(CH₂)₅—CH₂, 2.15 (s, 6, CH₃), 3.0–3.6 (m 6,

—CH₂—N—), 3.55 (d 2, —CH₂—O), 4.5 (m 1,

—CH—), 5.5 (s s 1, OH) 6.65 (s 3, ArH).

EXAMPLE 7

Preparation of 1-hexamethyleneimino-3-(2,6-dimethylanilino)-propanol-2

The mixture of 21.37 g (0.1 mole) of 1-xylidino-3-chloropropanol and 19.83 g (0.2 moles) of hexamethyleneimine is held at 140° C. for one hour. Then the solution thus obtained is diluted with 40 ml of ethyl acetate, and the separated hexamethyleneimine hydrochloride is filtered off. The hydrochloride is separated also from the filtrate with 50 ml of ethyl acetate containing 15% of hydrogen chloride.

Yield: 24.6 g (89.2%).

When recrystallized from ethanol, the product melts at 221° to 113° C.

Analysis: C₁₇H₂₈N₂O.2HCl (Mol. weight: 349.36): Calculated: C%=58.45 H%=8.66 N%=8.02 Cl=20.30; Found: C%=58.24 H%=8.69 N%=7.93 Cl%=20.26.

¹H-NMR (CDCl₃): 1.5–1.85 (m 4, —CH₂—(CH₂)₄—CH₂), 2.5 (s 6, CH₃), 2.8–3.7 (m 8, —CH₂—), 4.65 (s 1, OH), 4.45–4.85 (m 1,

—CH—), 6.9 (s 3 ArH).

EXAMPLE 8

Preparation of 1-(p-nitrophenoxy)-3-hexamethyleneiminopropanol-2

A mixture of 29.25 g (0.15 moles) of 1-(p-nitrophenoxy)-2,3-epoxypropane and 19.8 g (0.2 moles) of hexamethyleneimine is held at 140° to 145° C. for 3.5 hours. Then the excess of hexamethyleneimine is distilled off in vacuo. The residue solidifies in the form of yellow crystals.

Yield: 41.0 g (93%).

When recrystallized from ethyl acetate, the product melts at 63° to 65° C.

Analysis: C₁₅H₂₂N₂O₄ (Mol. weight: 294.36): Calculated: C%=61.21 H%=7.52 N%=9.52; Found: C%=61.37 H%=7.69 N%=9.45.

¹H-NMR (CDCl₃): 1.6 (s 8—(CH₂)₄—), 2.65 (m 6, —CH₂—N), 4.0 (d 3, —CH₂—O,

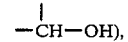

—CH—OH), 3.55 (d 1, OH), 6.85 (d 2, ArH), 8.0 (d 2, ArH).

EXAMPLE 9

Preparation of 1-(p-aminophenoxy)-3-hexamethyleneiminopropanol-2

The desired compound is obtained by subjecting the product prepared according to Example 8 to catalytic reduction.

Yield: 91% of oil.

¹H-NMR (CDCl₃) 1.55 (s 8, —CH₂), 2.6 (m 6, —CH₂—N), 3.8 (s 3, —CH₂—O, CH—O), 3.5 (s 3, NH, OH), 6.3, 6.43, 6.48, 6.65 (AB qa, 4 ArH).

The hydrochloride melts at 224° to 226° C.

EXAMPLE 10

Preparation of 1-(2,3-dichlorophenoxy)-3-hexamethyleneimino-propanol-2

A mixture of 21.9 g (0.1 mole) of 1-(2,3-dichlorophenoxy)-2,3-epoxypropane and 19.8 g (0.2 moles) of hexamethyleneimine is held at 140° to 145° C. for 5 hours. The excess of the imine is removed, the residual oil weighs 31.0 g (97.5%).

The product is dissolved in 50 ml of acetone, and 10 ml of methyl iodide are added. The weight of the separated methoiodide crystals is 25.3 g (55%). When recrystallized from ethanol, the product melts at 170° to 172° C.

Analysis: $C_{16}H_{24}Cl_2INO_2$ (Mol. weight: 460.2): Calculated: C%=41.76 H%=5.26 Cl%=15.41 I%=27.58 N%=3.0; Found: C%=41.82 H%=5.33 Cl%=15.32 I%=27.42 N%=3.0.

$^1$H-NMR (DMSO-d$_6$): 1.5–2.0 (m 8, —CH$_2$—(CH$_2$—)$_4$—CH$_2$), 3.1 (s 3, CH$_3$), 3.25–3.55 (m 6,

—CH$_2$—N—CH$_2$), 4.0 (d 2, —CH$_2$), 4.35 (m 1, CH), 5.65 (d 1, OH), 7.0 (s 3, ArH).

What we claim is:

1. A compound of the formula I

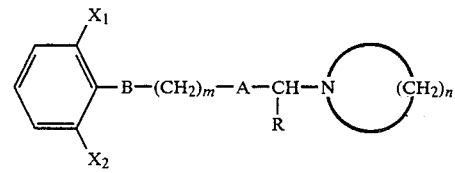

wherein
A is carbonyl or hydroxymethylene,
B is imino,
R is hydrogen or lower alkyl,
X$_1$ and X$_2$ are each lower alkyl,
n is 6 or 7, and
m is 0 or 1,
or a pharmaceutically acceptable acid addition, methyl iodide, or ethyl iodide salt thereof.

2. A compound of the formula I

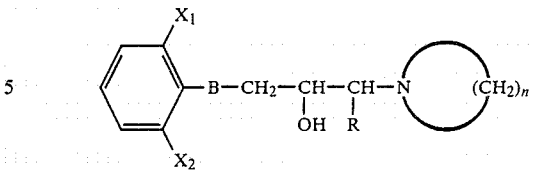

wherein
B is imino,
R is hydrogen or lower alkyl,
X$_1$ and X$_2$ are each lower alkyl, and
n is 6 or 7, or a pharmaceutically acceptable acid addition, methyl iodide or ethyl iodide salt thereof.

3. 1-hexamethyleneimino-3-(2,6-dimethylanilino)-2-propanol or a pharmaceutically acceptable acid addition, methyl iodide or ethyl iodide salt thereof as defined in claim 2.

4. A compound of the formula I

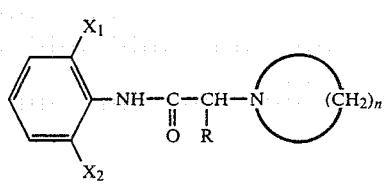

wherein
R is hydrogen or lower alkyl,
X$_1$ and X$_2$ are each lower alkyl, and
n is 6 or 7, or a pharmaceutically acceptable acid addition, methyl iodide, or ethyl iodide salt thereof.

5. An antiarrhythmic composition which consists essentially of a pharmaceutically effective amount of the compound of the formula I defined in claim 4, or a pharmaceutically acceptable acid addition salt, methyl iodide or ethyl iodide salt thereof, along with an inert, non-toxic, solid or liquid carrier.

6. A method of treating arrhythmia in a susceptible subject which comprises the step of administering an effective amount of the compound of the formula I defined in claim 1, or a pharmaceutically acceptable acid addition salt, methyl iodide or ethyl iodide salt thereof.

7. A method of treating arrhythmia in a susceptible subject which comprises the step of administering an effective amount of the compound of the formula I defined in claim 2, or a pharmaceutically acceptable acid addition salt, methyl iodide or ethyl iodide salt thereof.

8. A method of treating arrhythmia in a susceptible subject which comprises the step of administering an effective amount of the compound of the formula I defined in claim 4, or a pharmaceutically acceptable acid addition salt, methyl iodide or ethyl iodide salt thereof.

* * * * *